United States Patent
Lee et al.

[11] Patent Number: 5,637,690
[45] Date of Patent: Jun. 10, 1997

[54] SULFATE OF N-ACETYLNEURAMINIC ACID HOMOPOLYMER AND PROCESSES FOR MAKING AND USING THE SAME

[75] Inventors: Jang-ho Lee, Kawasaki; Yasuhiro Ota, Uji; Yoji Tsukada, Kyoto, all of Japan

[73] Assignee: Marukin Shoyu Co., Ltd., Kagawa, Japan

[21] Appl. No.: 313,227

[22] PCT Filed: Jan. 27, 1994

[86] PCT No.: PCT/JP94/00111

§ 371 Date: Dec. 27, 1994

§ 102(e) Date: Dec. 27, 1994

[87] PCT Pub. No.: WO94/17123

PCT Pub. Date: Aug. 4, 1994

[30] Foreign Application Priority Data

Jan. 29, 1993 [JP] Japan .................. 5-014117
Apr. 27, 1993 [JP] Japan .................. 5-101290

[51] Int. Cl.$^6$ .................. C07H 11/00; C07H 13/12
[52] U.S. Cl. .................. 536/118; 536/122; 536/123.1
[58] Field of Search .................. 536/118, 122, 536/123.1; 514/54, 885

[56] References Cited

U.S. PATENT DOCUMENTS 5,273,892  12/1993  Okutani .................. 536/118
5,447,919  9/1995   Hosang et al. .................. 536/118

Primary Examiner—Nathan M. Nutter
Attorney, Agent, or Firm—Knobbe, Martens, Olson & Bear, LLP

[57] ABSTRACT

A sulfate ester of N-acetylneuraminic acid homopolymer represented by the formula (I) or a pharmaceutically acceptable salt thereof:

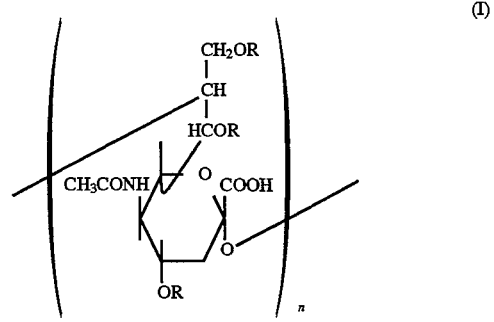

wherein R represents H or $SO_3H$, n is 5–1,000, wherein the number of $SO_3H$ residues per 1 molecule of N-acetylneuraminic acid residues is 0.1 to 3.0, which sulfate ester demonstrates anti-HIV activity.

17 Claims, No Drawings

SULFATE OF N-ACETYLNEURAMINIC ACID HOMOPOLYMER AND PROCESSES FOR MAKING AND USING THE SAME

FIELD OF THE INVENTION

The invention relates to a sulfate ester of N-acetylneuraminic acid homopolymer, a method for producing the same, a medicament effective for treating human immunodeficiency virus (HIV) comprising the sulfate ester as an active ingredient (anti-HIV agent), a method for treating AIDS using the sulfate ester, the sulfate ester for use to treat AIDS and use of the sulfate ester to produce the medicament.

BACKGROUND ART

Although the number of patient of Acquired Immune Deficiency Syndrome (AIDS) caused by HIV is rapidly increasing, an effective method for treating AIDS has not been established yet. Because of high mortality thereof after crisis, there is an urgent demand for searching an anti-HIV agent.

Azidothymidine and like reverse transcriptase inhibitors, and heparin and like sulfated polysaccharides capable of suppressing infection of HIV to a target cell are exemplified as a known anti-HIV agent (see, Japanese unexamined patent publication Nos. 215529/1987; 7577/1990; and 91027/1992).

Although azidothymidine and like reverse transcriptase inhibitors inhibit increase of HIV, the inhibitors have a strong side effect because of an action thereof on a nucleic acid synthesis. A long-term administration is, therefore, difficult. In contrast, heparin and like sulfated polysaccharides having been used as an anticoagulant have a strong anticoagulant activity relative to an anti-HIV activity. The sulfated polysaccharides have a very strong anticoagulant activity at a concentration where the polysaccharides exhibit an anti-HIV activity. Development of the sulfated polysaccharides as an anti-HIV agent is difficult due to the side effect thereof (anticoagulant activity).

It is an object of the present invention to provide a medicament having an excellent anti-HIV activity and being free of a side effect.

DISCLOSURE OF THE INVENTION

The inventors conducted extensive research in considering the problems of the prior art, and found that a novel sulfate ester of N-acetylneuraminic acid homopolymer is very weak in side effects, such as an anticoagulant activity, at a dose of exhibiting an anti-HIV activity.

Thus, the invention provides a sulfate ester of N-acetylneuraminic acid homopolymer represented by the following formula (I):

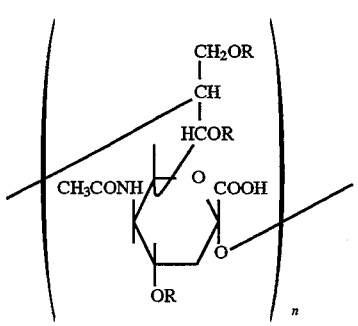

[wherein R represents, the same or different, a hydrogen atom or $SO_3H$, n is an integer of 5 to 1,000, provided that the number of $SO_3H$ residue per 1 molecule of N-acetylneuraminic acid residue is 0.1 to 3.] and a pharmaceutically acceptable salt thereof.

Further, the invention provides a method for producing a sulfate ester of N-acetylneuraminic acid homopolymer represented by the following formula (I):

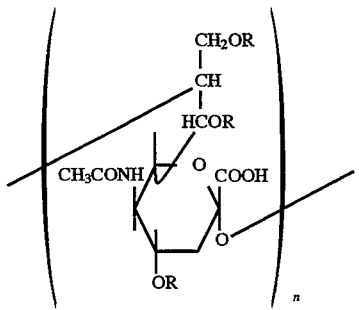

[wherein R and n are as defined above provided that the number of $SO_3H$ residue per 1 molecule of N-acetylneuraminic acid residue is 0.1 to 3.] and a pharmaceutically acceptable salt thereof characterised in that 1 part by weight of N-acetylneuraminic acid homopolymer is reacted with 0.5 to 200 parts by weight of a catalyst and 0.2 to 30 parts by weight of a sulfating agent in the presence or absence of a solvent.

Further, the invention provides an anti-HIV agent comprising a sulfate ester of N-acetylneuraminic acid homopolymer represented by the following formula (I):

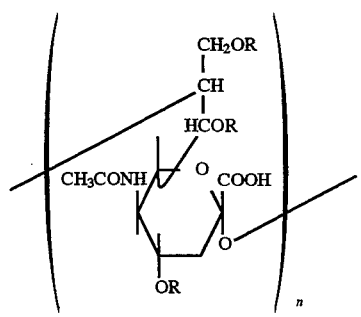

[wherein R and n are as defined above provided that the number of $SO_3H$ residue per 1 molecule of N-acetylneuraminic acid residue is 0.1 to 3.] or a pharmaceutically acceptable salt thereof combined with an additive.

Furthermore, the invention provides a method for treating AIDS characterised in that the method comprises administering a sulfate ester of N-acetylneuraminic acid homopolymer represented by the following formula (I):

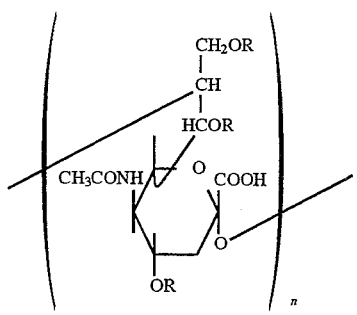

[wherein R and n are as defined above provided that the number of $SO_3H$ residue per 1 molecule of N-acetylneuraminic acid residue is 0.1 to 3.] or a pharmaceutically acceptable salt thereof to a patient.

Furthermore, the invention provides a sulfate ester of N-acetylneuraminic acid homopolymer represented by the following formula (I):

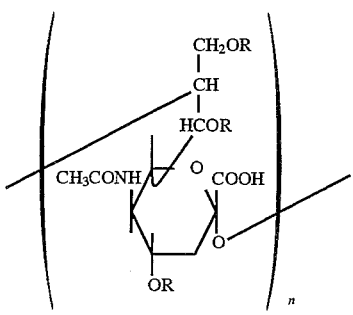

[wherein R and n are as defined above provided that the number of $SO_3H$ residue per 1 molecule of N-acetylneuraminic acid residue is 0.1 to 3.] or a pharmaceutically acceptable salt thereof for use as a medicament.

Furthermore, the invention provides use of a sulfate ester of N-acetylneuraminic acid homopolymer represented by the following formula (I):

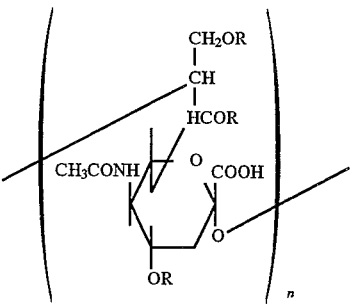

[wherein R and n are as defined above provided that the number of $SO_3H$ residue per 1 molecule of N-acetylneuraminic acid residue is 0.1 to 3.] or a pharmaceutically acceptable salt thereof to produce a medicament for treating AIDS.

With respect to the compound of formula (I), the number of $SO_3H$ residue represented by R per 1 mole of N-acetylneuraminic acid residue is 0.1 to 3, preferably 0.3 to 1.5, most preferably 0.5 to 1.0.

With respect to the compound of formula (I), n is an integer of 5 to 1,000, preferably an integer of 6 to 200, most preferably an integer of 6 to 70. The sulfate ester of N-acetylneuraminic acid homopolymer is a single compound in which n is only one kind, or a mixture of the plural sulfate esters of N-acetylneuraminic acid homopolymer in which each n is different within the range of 5 to 1,000.

The novel sulfate ester of the invention can be produced according to the following method wherein 1 part by weight of N-acetylneuraminic acid homopolymer is reacted with 0.5 to 200 parts by weight of a catalyst and 0.2 to 30 parts by weight of a sulfating agent in the presence or absence of a solvent. Reaction time is about 0.2–100 hours, and reaction temperature is about 0°–90° C. The catalyst includes pyridine, dimethylaminopyridine, triethylamine, etc. The sulfating agent includes chlorosulfuric acid, piperidine sulfate, sulfur trioxide trimethylamine complex, sulfur trioxide pyridine complex, etc. When using pyridine, etc. as a catalyst in an excessive amount, there is no need to use a solvent. It is not necessary to use a solvent. However, dimethylformamide, dimethylsulfoxide, formamide, etc. are exemplified as a solvent, when a solvent is employed. N-acetylneuraminic acid homopolymer used as a starting material is not specifically limited to, but includes a homopolymer having a constant polymerization degree and a mixture of natural acetylneuraminic acid homopolymer, such as colominic acid.

The following is a structure of N-acetylneuraminic acid homopolymer which is a starting material:

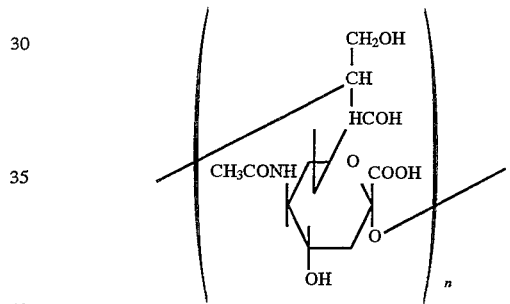

[wherein n is as defined above.]

After completion of the sulfating reaction, a sulfated polysaccharide can be purified by a known method, such as concentration, gel filtration chromatography, ion-exchange chromatography, reprecipitation, dialysis, etc.

In the invention, "pharmaceutically acceptable salts" include sodium, potassium, lithium and like alkali metal salt, magnesium, calcium and like alkaline earth metal salts. The salts can be produced by neutralizing a reaction mixture of sulfating reaction using sodium hydroxide, potassium carbonate, etc. The salts can also be prepared by isolating sulfated polysaccharide as a free acid, followed by converting the acid to a salt according to a conventional method.

The sulfate ester of N-acetylneuraminic acid homopolymer of formula (I) of the invention combined with a variety of pharmaceutically acceptable additives can be used as an anti-HIV agent. The medical composition is not specifically limited to, but used, for example, as injections, tablets, capsules, granules, fine granules, emulsions and like oral preparations, injections, suppositories, etc.

When preparing an anti-HIV agent, as injections, comprising the sulfate ester of N-acetylneuraminic acid homopolymer as an active ingredient, the additives include a pH-adjusting agent, buffer, stabilizer, isotonic agent, local anesthetic, etc., which are suitably formulated to prepare injections. The injections are administered intravenously, intramuscularly, subcutaneously or intraperitoneally.

When the anti-HIV agent is prepared as oral preparations, the additives include excipient, disintegrators, lubricants, binders, flavors, corrigents, etc.

When the anti-HIV agent is prepared as suppositories, the additives include bases, surfactants, etc.

The additives include all additives used for preparing each formulation and are employed in a suitable amount.

The amount of active ingredient, i.e., the sulfate ester of N-acetylneuraminic acid homopolymer combined in each formulation per each unit dosage varies with the patient's age, sex, body weight, symptoms, but is generally about 1–100 mg in oral preparations, about 0.1–20 mg in injections, about 1–50 mg in suppositories. The daily clinical dosage for human adult varies with a type of formulations, but is about 1–1,000 mg, preferably about 10–200 mg.

The anti-HIV agent can be used for prevention of HIV-infection by applying the agent to vulva, vagina or penis before a sexual act.

The novel sulfate ester of N-acetylneuraminic acid homopolymer of the invention has a similar anti-HIV activity relative to known sulfated polysaccharides, and is free of a side effect, such as an anticoagulant activity which has been a problem. The sulfate ester of the invention with a low cytotoxicity, is useful for preventing and curing HIV and can be administered for a long time.

EXAMPLES

The invention will be described below in greater detail using examples and pharmacological tests, but the invention is not limited to the examples etc.

In the examples and comparative examples, the following measuring equipment were used.

(1) HPLC

Column: Shodex OHpak KB-803 (product of SHOWA DENKO Co.)

Standard: polyethyleneoxide (product of TOSO Co., Ltd, Molecular weight 26,000 and 46,000) and polyethyleneglycol (product of NACALAI TESQUE INC.; Molecular weight 8,300).

(2) Determination of sulfate group

A sulfate group was determined according to the Dodgson method described in *Biochem. J.*, 78, 312 (1961).

(3) Determination of N-acetylneuraminic acid

N-acetylneuraminic acid was determined by Resorcin hydrochloride method described in J. T. Cassidy et al., *J. Biol. Chem.*, 240, 3501 (1965).

(4) IR

IR was determined by KBr method using SHIMADZU Infrared Spectrophotometer IR-400.

EXAMPLE 1

Production of sulfate ester of N-acetylneuraminic acid homopolymer (1)

A 100 ml of dry pyridine was added to a three-necked flask and 10 ml of chlorosulfuric acid was added dropwise to the flask with ice-cooling for 30–40 minutes. After adding formamide (5 ml) solution of colominic acid (obtained from NACALAI TESQUE INC.) (626 mg) to the solution, the reaction mixture was stirred at 70° C. for 1 hour. After neutralizing the reaction mixture at pH 7 by adding 5N-NaOH, the mixture was dialyzed for 3 days against running water using a dialysis tube (trademark: Cellotube, product of VISKASE SALES CORP., pore diameter=24 Å). A 900 mg of a desired sulfate ester was obtained as a powder by concentrating a solution in the dialysis tube using a rotary evaporator at 40° C. or less to a volume of 10 ml, followed by lyophilizing the concentrated residue.

A sulfate content of the ester thus obtained was determined by the Dodgson method, showing that the ester has a sulfate content of 30% by weight.

EXAMPLE 2

Production of sulfate ester of N-acetylneuraminic acid homopolymer (2)

About 850 mg of a desired sulfate ester as a powder was obtained according to the same procedure as shown in Example 1 except that the reaction time and reaction temperature were 55° C. and 2 hours, respectively A sulfate content of the ester thus obtained was determined by the Dodgson method showing that the ester has a sulfate content of 10% by weight.

Pharmacological Test 1

Anti-HIV activity

A medium in which MT-4 cell [Miyoshi I. et al., *Gann Monogr.*, 28, 219–228 (1982)] was included in a proportion of $2 \times 10^5$ cell/ml medium (RPMI-1640+10%FCS) was prepared. To each of 500 µl portion of the medium were added sulfated colominic acid obtained from examples 1 and 2 at a concentration shown in table 1. After two hours addition of the esters, HIV was infected to cells in each well in the proportion of $5 \times 10^3$ PFU/well. After 4 days from HIV infection, smear of MT-4 cell was prepared to detect HIV antigen positive cells by immunofluorescence (Harada S. et al., *Science*, 229, 563–566 (1985); Takeuchi Y., et al., *Jpn. J. Cancer Res.* (Gann), 78, 11–15 (1987)).

A proportion of virus-infected cells (HIV antigen positive cells) (%) are shown in table 1. An anti-HIV activity of colominic acid which is a starting material in place of sulfated colominic acid was determined in the same manner as above. The results are shown in table 2.

In tables 1 and 3, a sample having a concentration of sulfated colominic acid of zero was regarded as control. In table 2, "—" indicates no toxicity.

TABLE 1

| Final concentration of sulfated colominic acid (µg/ml) | 1 | 0.2 | 0 |
| --- | --- | --- | --- |
| Sample from Example 1 Cell Infection Ratio (%) | <5 | 50 | >95 |
| Sample from Example 2 Cell Infection Ratio (%) | <5 | 50 | >95 |

TABLE 2

| Final concentration of colominic acid (µg/ml) | 0 | 1 | 3 | 10 | 30 | 100 |
| --- | --- | --- | --- | --- | --- | --- |
| Cell Infection Ratio (%) | >95 | >95 | >95 | >95 | >95 | >95 |
| Cytotoxicity | — | — | — | — | — | — |

Tables 1 and 2 clearly demonstrate that the anti-HIV agent of the invention can suppress HIV infection at a concentration of 0.2 µg/ml significantly and that free coliminic acid does not have an anti-HIV activity.

Pharmacological Test 2
Cytotoxicity

A cytotoxicity of sulfated colominic acid was assayed in the same manner as Pharmacological Test 1. Specifically, after MT-4 cell prepared at a concentration of $1 \times 10^5$ cell/ml was cultured for 4 days in the presence of a variety of concentrations of sulfated colominic acid, the number of cells was counted. Cytotoxicity was evaluated by calculating a cell survival ratio in each final concentration of sulfated colominic acid taking as 100% the cell survival ratio of control, in which final concentration of sulfated colominic acid is zero.

The results are shown in table 3.

TABLE 3

| Final concentration of sulfated colominic acid (μg/ml) | 100 | 10 | 1 | 0 |
|---|---|---|---|---|
| Sample from Example 1 Cell Survival Ratio (%) | 102 | 101 | 102 | 100 |
| Sample from Example 2 Cell Survival Ratio (%) | 101 | 101 | 102 | 100 |

Table 3 clearly demonstrates that the anti-HIV agent of the invention has substantially no cytotoxicity within the above-mentioned range of the concentration.

Pharmacological Test 3

In order to determine the minimum number of monomer unit of N-acetylneuraminic acid homopolymer, sulfate esters of formula (I) in which n is 1–6 were produced. A cytotoxicity and an anti-HIV activity of each sulfate ester were determined in the same manner as pharmacological tests 1 and 2. The results are shown in table 4. In table 4:

DP-6-S represents a sulfate ester of N-acetylneuraminic acid hexamer (n=6). DP-2-S to DP-5-S similarly represent sulfate ester of N-acetylneuraminic acid dimer to pentamer (n=2–5). NANA-S represents a sulfate ester monomer (n=1).

Further, in a column of toxicity, "—" demonstrate no cytotoxicity or no anti-HIV activity.

TABLE 4

| Agent | | Final concentration (μg/ml) | | | | | | | Control | $IC_{50}$ (μg/ml) |
|---|---|---|---|---|---|---|---|---|---|---|
| | | 100 | 30 | 10 | 3 | 1 | 0.3 | 0.1 | | |
| DP-6-S | Toxicity | — | — | — | — | — | — | — | — | 20 |
| | Cell infection ratio (%) | <5 | 30 | 80 | >95 | >95 | >95 | >95 | >95 | |
| DP-5-S | Toxicity | — | — | — | — | — | — | — | — | 30 |
| | Cell infection ratio (%) | 10 | 40 | >95 | >95 | >95 | >95 | >95 | >95 | |
| DP-4-S | Toxicity | — | — | — | — | — | — | — | — | 100 |
| | Cell infection ratio (%) | 50 | 80 | >95 | >95 | >95 | >95 | >95 | >95 | |
| DP-3-S | Toxicity | — | — | — | — | — | — | — | — | — |
| | Cell infection ratio (%) | >95 | >95 | >95 | >95 | >95 | >95 | >95 | >95 | |
| DP-2-S | Toxicity | — | — | — | — | — | — | — | — | — |
| | Cell infection (%) ratio (%) | >95 | >95 | >95 | >95 | >95 | | | >95 | |
| NANA-S | Toxicity | — | — | — | — | — | — | — | — | — |
| | Cell infection ratio (%) | >95 | >95 | >95 | >95 | >95 | | | >95 | |

Table 4 clearly demonstrates that pentamer or more of sulfated N-acetylneuraminic acid homopolymers represent an anti-HIV activity.

Pharmacological Test 4
Anticoagulant activity

Activated partial thromboplastin time (APTT) of sulfated colominic acids prepared in examples 1 and 2, colominic acid (starting material), dextran sulfate (average molecular weight: 15,000, Genzyme Co., Ltd.) and distilled water (control) was determined by using an APTT measuring reagent (PLATELIN EXCEL LS; ORGANON TEKNIKA Co., Ltd). The results are shown in Table 5. Components of PLATELIN EXCEL LS are shown below.

Major components of PLATELIN EXCEL LS in 1 vial:
Phospholipid of hen yolk: 0.6 mg
Phospholipid of bovine brain: 0.12 mg
light silicic acid anhydride: 6 mg

TABLE 5

| Anti-HIV agent | APTT time (sec) |
|---|---|
| Sulfated colominic acid from Example 1 (50 μg/ml) | 45 |
| Sulfated colominic acid from Example 2 (50 μg/ml) | 45 |
| Colominic acid (50 μg/ml) | 45 |
| Dextran sulfate (50 μg/ml) | 90 |
| Control (distilled water) | 45 |

The sulfated colominic acid of the invention do not demonstrate anticoagulant activity at a concentration of 50 μg/ml which is higher than the concentration at which the sulfated colominic acid exhibit an anti-HIV activity. In contrast, dextran sulfate exhibit a high anticoagulant activity.

What we claim is:

1. A sulfate ester of N-acetylneuraminic acid homopolymer represented by the formula (I) or a pharmaceutically acceptable salt thereof:

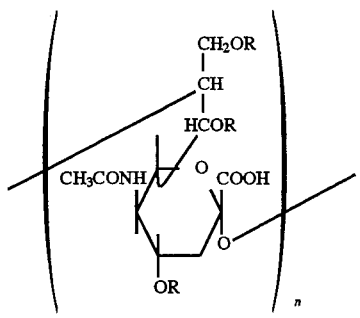

(I)

wherein each R represents independently a hydrogen atom or —$SO_3H$, and n is an integer of 5 to 1,000, provided that the number of $SO_3H$ residues per 1 molecule of N-acetylneuraminic acid residues is 0.1 to 3.0.

2. The sulfate ester of N-acetylneuraminic acid homopolymer as defined in claim 1, wherein n is an integer of 6 to 200.

3. The sulfate ester of N-acetylneuraminic acid homopolymer as defined in claim 2, wherein n is an integer of 6 to 70.

4. The sulfate ester of N-acetylneuraminic acid homopolymer as defined in claim 1, wherein the number of $SO_3H$ residues per 1 molecule of N-acetylneuraminic acid residues is 0.3 to 1.5.

5. The sulfate ester of N-acetylneuraminic acid homopolymer as defined in claim 1, wherein the number of $SO_3H$ residues per 1 molecule of N-acetylneuraminic acid residues is 0.5 to 1.0.

6. A method for producing a sulfate ester of N-acetylneuraminic acid homopolymer represented by the following formula (I):

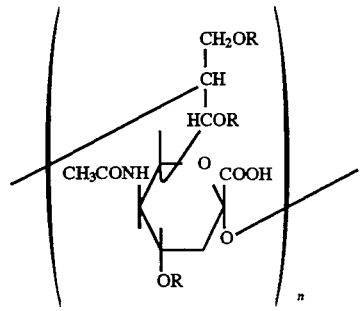

(I)

wherein each R represents independently a hydrogen atom or —$SO_3H$, and n is an integer of 5 to 1,000, provided that the number of $SO_3H$ residues per 1 molecule of N-acetylneuraminic acid residues is 0.1 to 3.0, comprising reacting 1 part by weight of N-acetylneuraminic acid homopolymer with 0.5 to 200 parts by weight of a catalyst and 0.2 to 30 parts by weight of a sulfating agent in the presence or absence of a solvent.

7. The method as defined in claim 6, wherein the catalyst is pyridine, dimethylaminopyridine or triethylamine.

8. The method as defined in claim 6, wherein the sulfating agent is chlorosulfuric acid, piperidine sulfate, sulfur trioxide trimethylamine complex or sulfur trioxide pyridine complex.

9. The method as defined in claim 6, wherein n is an integer of 6 to 200.

10. The method as defined in claim 9, wherein n is an integer of 6 to 70.

11. The method as defined in claim 6, wherein the number of $SO_3H$ residues per 1 molecule of N-acetylneuraminic acid residues is 0.3 to 1.5.

12. The method as defined in claim 11, wherein the number of $SO_3H$ residues per 1 molecule of N-acetylneuraminic acid residues is 0.5 to 1.0.

13. An anti-HIV agent comprising a sulfate ester of N-acetylneuraminic acid homopolymer represented by the following formula (I) or a pharmaceutically acceptable salt thereof:

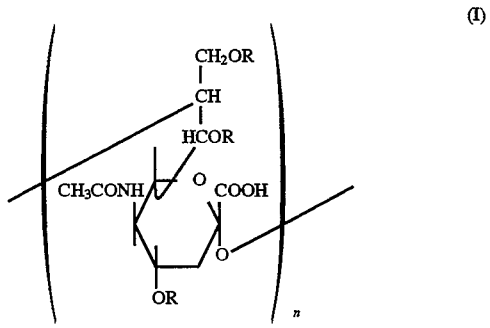

(I)

wherein each R represents independently a hydrogen atom or —$SO_3H$, and n is an integer of 5 to 1,000, provided that the number of $SO_3H$ residues per 1 molecule of N-acetylneuraminic acid residues is 0.1 to 3.0.

14. The anti-HIV agent as defined in claim 13, wherein n is an integer of 6 to 200.

15. The anti-HIV agent as defined in claim 14, wherein n is an integer of 6 to 70.

16. The anti-HIV agent as defined in claim 13, wherein the number of $SO_3H$ residues per 1 molecule of N-acetylneuraminic acid residues is 0.3 to 1.5.

17. The anti-HIV agent as defined in claim 13, wherein the number of $SO_3H$ residues per 1 molecule of N-acetylneuraminic acid residues is 0.5 to 1.0.

* * * * *